(12) United States Patent
O'Brien et al.

(10) Patent No.: US 11,731,076 B1
(45) Date of Patent: Aug. 22, 2023

(54) MEMBRANE PROCESS AND SYSTEM FOR HIGH RECOVERY OF A NONPERMEATING GAS UTILIZING A SWEEP GAS

(71) Applicant: Air Products and Chemicals, Inc., Allentown, PA (US)

(72) Inventors: Matthew P. O'Brien, House Springs, MO (US); Donald E. Henry, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 17/956,933

(22) Filed: Sep. 30, 2022

(51) Int. Cl.
  *B01D 53/22* (2006.01)
  *C07C 7/00* (2006.01)
  *C07C 7/144* (2006.01)

(52) U.S. Cl.
  CPC ......... *B01D 53/226* (2013.01); *B01D 53/227* (2013.01); *C07C 7/005* (2013.01); *C07C 7/144* (2013.01)

(58) Field of Classification Search
  CPC ....... C07C 7/144; C07C 7/005; B01D 53/226; B01D 53/227
  See application file for complete search history.

(56) References Cited

U.S. PATENT DOCUMENTS

| 10,254,041 B2 | 4/2019 | Van Roosmalen |
| 11,285,434 B2 | 3/2022 | Henry |
| 2004/0045432 A1* | 3/2004 | Yamamoto ............. B01D 53/22 95/48 |
| 2018/0251694 A1 | 9/2018 | Foody et al. |

* cited by examiner

*Primary Examiner* — Thuan D Dang
(74) *Attorney, Agent, or Firm* — Amy C. Trexler

(57) ABSTRACT

A method for separating a raw feed gas stream using a plurality of membrane module stages. The raw feed gas stream may be from a biogas process. Off-gas from another unit process in the system, such as a temperature swing adsorption unit or liquefaction unit, may be used as a low pressure sweep gas on the low pressure side of at least one of the membrane module stages. In one example, the sweep gas is used in a first membrane module stage. In another example, a stripping membrane module stage is provided and the sweep gas is used in the stripping membrane module stage. Optionally, portions of the off-gas could be directed to other streams in the system for the purpose of balancing compressor power requirements.

20 Claims, 6 Drawing Sheets

Stream Compositions – System 10 of FIG. 1

| Stream Number | 30 | 48 | 32 | 36 | 40 | 42 | 46 | 44 | 18 | 50 | 38 | Summary |
|---|---|---|---|---|---|---|---|---|---|---|---|---|
| Composition (mol%) | | | | | | | | | | | | |
| CH4 | 60.00 | 56.12 | 69.61 | 67.69 | 35.60 | 35.60 | 5.96 | 62.17 | 95.00 | 1.00 | 98.50 | Sales Gas |
| CO2 | 40.00 | 43.88 | 30.39 | 32.31 | 64.40 | 64.40 | 94.04 | 37.83 | 5.00 | 99.00 | 1.50 | CO2 mol% 1.50 |
| O2 | | | | | | | | <1 PPM | | | | CH4 Rec 99.58 |
| N2 | | | | | | | | <1 PPM | | | | (Includes TSA off Gas CH4) |
| H2O | | | nil | | | | nil | | | | | |
| Compres Oil | | | | | | | | | | | | |
| Total | 100.00 | 100.00 | 100.00 | 100.00 | 100.00 | 100.00 | 100.00 | 100.00 | 100.00 | 100.00 | 100.00 | |
| Molecular Weight | 27.23 | 28.31 | 24.54 | 25.08 | 34.05 | 34.05 | 42.34 | 26.62 | 17.44 | 43.73 | 16.46 | |
| Total Flow: | | | | | | | | | | | | |
| Nm3/hr | 500.0 | 20.2 | 720.2 | 971.1 | 475.7 | 475.7 | 224.9 | 250.8 | 200.0 | 204.6 | 495.4 | |
| kgmol/hr | 22.31 | 0.90 | 32.13 | 43.32 | 21.22 | 21.22 | 10.03 | 11.19 | 8.92 | 9.13 | 22.10 | |
| kg/hr | 607.4 | 25.6 | 788.6 | 1086.6 | 722.7 | 722.7 | 424.8 | 297.9 | 155.6 | 399.2 | 363.8 | |
| Temperature °C | 40.0 | 20.0 | 39.6 | 40.0 | 40.0 | 40.0 | 40.0 | 31.8 | 40.0 | 39.4 | 32.9 | |
| Pressure bar g | 0.0 | 0.9 | 0.0 | 13.00 | 0.98 | 13.90 | 2.73 | 13.90 | 0.89 | 0.00 | 13.00 | |

FIG. 4

Stream Compositions – System 100 of FIG. 2

| Stream Number | 130 | 148 | 132 | 136 | 140 | 142 | 146 | 144 | 118 | 150 | 138 | Summary |
|---|---|---|---|---|---|---|---|---|---|---|---|---|
| Composition (mol%) | | | | | | | | | | | | Sales Gas |
| $CH_4$ | 60.00 | 46.85 | 59.28 | 59.42 | 41.85 | 41.85 | 6.65 | 59.57 | 95.00 | 1.00 | 98.50 | $CO_2$ mol%   1.50 |
| $CO_2$ | 40.00 | 53.15 | 40.72 | 40.58 | 58.15 | 58.15 | 93.35 | 40.43 | 5.00 | 99.00 | 1.50 | $CH_4$ Rec.  99.58 |
| $O_2$ | | | | | | | | <1 PPM | | | | (Includes TSA off Gas $CH_4$) |
| $N_2$ | | | | | | | | | | | | |
| $H_2O$ | | | nil | | | | nil | <1 PPM | | | | |
| Compres Oil | | | | | | | | <1 PPM | | | | |
| Total | 100.00 | 100.00 | 100.00 | 100.00 | 100.00 | 100.00 | 100.00 | 100.00 | 100.00 | 100.00 | 100.00 | |
| Molecular Weight | 27.23 | 30.91 | 27.43 | 27.39 | 32.31 | 32.31 | 42.15 | 27.35 | 17.44 | 43.73 | 16.46 | |
| Total Flow: | | | | | | | | | | | | |
| Nm3/hr | 500.0 | 28.8 | 528.8 | 992.2 | 696.8 | 696.8 | 233.4 | 463.4 | 200.0 | 204.6 | 495.4 | |
| kgmol/hr | 22.31 | 1.28 | 23.59 | 44.27 | 31.09 | 31.09 | 10.41 | 20.68 | 8.92 | 9.13 | 22.10 | |
| kg/hr | 607.4 | 39.7 | 647.1 | 1,212.6 | 1,004.3 | 1,004.3 | 438.8 | 565.5 | 155.6 | 399.2 | 363.8 | |
| Temperature °C | 40.0 | 22.8 | 39.0 | 40.0 | 40.0 | 40.0 | 40.0 | 35.4 | 40.0 | 40.0 | 316 | |
| Pressure bar g | 0.0 | 0.5 | 0.0 | 13.00 | 0.80 | 13.90 | 2.54 | 13.90 | 0.89 | 0.00 | 13.00 | |

FIG. 5

MEMBRANE PROCESS AND SYSTEM FOR HIGH RECOVERY OF A NONPERMEATING GAS UTILIZING A SWEEP GAS

BACKGROUND

This application relates to a multi-stage membrane process and system for methane recovery from biogas.

Multi-stage membrane systems are a known method to upgrade raw biogas streams into high purity methane streams. Such multi-stage membrane systems can achieve high methane recovery and purity, but often require relatively high membrane areas (or counts) to do so.

In some membrane-based biogas separation processes, there are also low pressure off-gases with low carbon dioxide (CO2) concentration generated from other unit operations such as tail gases from thermal swing adsorption (TSA) systems or liquefaction units. It may be desirable to insert the low pressure off-gas in the separation process. For example, it may be desirable to recover methane (CH4) or CO2 from the off-gas stream. However, inserting the off-gas stream into the separation process may increase the membrane area required to achieve the desired product purity.

Therefore, there is a need for an effective, reliable and cost-efficient multi-stage membrane method and system that can achieve a desired methane product recovery and purity while reducing the required membrane size and capital cost. Also, there is a need for treating external gas streams generated from other unit operations utilizing a multi-stage membrane method system that does not increase membrane area and associated capital cost.

SUMMARY

This summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The disclosed embodiments satisfy the need in the art by providing a multi-stage membrane method and system for methane recovery from biogas that utilizes a gas to sweep the membrane responsible for generating the final biomethane product. The sweep gas is applied along the low pressure (or permeate) side of the membrane and serves to dilute the partial pressure of the species being permeated on the low pressure side and increase the driving force, which improves performance of the membrane process and reduces membrane capital cost.

Several aspects of the systems and methods are outlined below.

Aspect 1: A method comprising:
(a) compressing a feed gas stream to form a pressurized feed gas stream;
(b) feeding the pressurized feed gas stream into at least one first stage membrane module, each of the at least one first stage membrane module having a first high pressure side and a first low pressure side, the first high pressure side extending from a first feed port to a first non-permeate port, the first low pressure side being in fluid flow communication with a first sweep port and a first permeate port;
(c) separating the pressurized feed gas stream in each of the at least one first stage membrane module into a first non-permeate stream and a first permeate stream;
(d) sweeping and discharging the first permeate stream from the first permeate port using a sweep gas that is fed in a first direction of flow that is countercurrent to a second direction of flow that the pressured feed gas stream is fed into the at least one first stage membrane module in step (a);
(e) discharging the first non-permeate stream from each of the at least one first stage membrane module through the first non-permeate port;
(f) compressing the first permeate stream in a first compressor to form a compressed first permeate stream;
(g) feeding the compressed first permeate stream to at least one second stage membrane module, each of the at least one second stage membrane module having a second high pressure side and a second low pressure side, the second high pressure side extending from a second feed port to a second non-permeate port, the second low pressure side being in fluid flow communication with a second sweep port and a second permeate port;
(h) separating the compressed first permeate stream in the at least one second stage membrane module into a second non-permeate stream and a second permeate stream;
(i) discharging the second non-permeate stream from each of the at least one second stage membrane module through the second non-permeate port;
(j) discharging the second permeate stream from each of the at least one second stage membrane module through the second permeate port;
(k) combining the second non-permeate stream with a compressed combined feed stream to form the pressurized feed gas stream;
(l) feeding the second permeate stream into at least one third stage membrane module, each of the at least one third stage membrane module having a third high pressure side and a third low pressure side, the third high pressure side extending from a third feed port to a third non-permeate port, the third low pressure side being in fluid flow communication with a third sweep port and a third permeate port;
(m) separating the second permeate stream in the at least one third stage membrane module into a third non-permeate stream and a third permeate stream;
(n) discharging the third non-permeate stream from each of the at least one third stage membrane module through the third non-permeate port;
(n) discharging the third permeate stream from each of the at least one third stage membrane module through the third permeate port;
(o) combining the third non-permeate stream with a raw feed gas stream to form a combined feed stream; and
(p) compressing the combined feed stream in a second compressor to form the compressed combined feed stream.

Aspect 2: The method of Aspect 1, wherein step (d) further comprises introducing the sweep gas at a pressure of less than 1.00 barg.

Aspect 3: The method of any of Aspects 1-2, wherein the sweep gas comprises less than 15% carbon dioxide Aspect 4: The method of any of Aspects 1-3, wherein the sweep gas comprises at least 85% methane.

Aspect 5: The method of any of Aspects 1-4, wherein the sweep gas provides a first molar flow rate of nitrogen that is less than or equal to 5% of a second molar flow rate of the pressurized feed gas stream.

Aspect 6: The method of any of Aspects 1-5, wherein the sweep gas comprises an off-gas.

Aspect 7: The method of any of Aspects 1-6, wherein the off-gas comprises an off-gas from a liquefaction process or a temperature swing adsorption process.

Aspect 8: The method of any of Aspects 1-7, wherein the sweep gas comprises a tail gas from a thermal swing adsorption (TSA) process.

Aspect 9: The method of any of Aspects 1-8, further comprising directing at least a portion of the off-gas to one or more selected from the group of: (1) the feed gas stream and (2) the first permeate stream.

Aspect 10: The method of any of Aspects 1-9, wherein the at least one first stage membrane module comprises a plurality of membrane modules arranged in series and/or parallel.

Aspect 11: The method of any of Aspects 1-10, wherein the at least one second stage membrane module comprises a plurality of membrane modules arranged in series and/or parallel.

Aspect 12: The method of any of Aspects 1-11, wherein the at least one third stage membrane module comprises a plurality of membrane modules arranged in series and/or parallel.

Aspect 13: The method of any of Aspects 1-12, wherein the raw feed gas stream is a product stream from an anaerobic digester.

Aspect 14: The method of any of Aspects 1-13, wherein the raw feed gas stream comprises at least 40% methane.

Aspect 15: The method of any of Aspects 1-14, wherein step (f) further comprises compressing the first permeate stream in the first compressor to a pressure of at least 10 barg to form the compressed first permeate stream.

Aspect 16: The method of any of Aspects 1-15, wherein the first non-permeate stream comprises at least 70% methane.

Aspect 17: The method of any of Aspects 1-16, wherein the third permeate stream comprises less than 1% methane.

Aspect 18: A method comprising:
(a) compressing a feed gas stream to form a pressurized feed gas stream;
(b) feeding the pressurized feed gas stream into at least one first stage membrane module, each of the at least one first stage membrane module having a first high pressure side and a first low pressure side, the first high pressure side extending from a first feed port to a first non-permeate port, the first low pressure side being in fluid flow communication with a first sweep port and a first permeate port;
(c) separating the pressurized feed gas stream in each of the at least one first stage membrane module into a first non-permeate stream and a first permeate stream;
(d) discharging the first non-permeate stream from each of the at least one first stage membrane module through the first non-permeate port;
(e) feeding the first non-permeate stream into at least one stripping membrane module, each of the at least one stripping membrane module having a fourth high pressure side and a fourth low pressure side, the fourth high pressure side extending from a fourth feed port to a fourth non-permeate port, the fourth low pressure side being in fluid flow communication with a fourth permeate port;
(f) separating the first non-permeate stream in each of the at least one stripping membrane module into a fourth non-permeate stream and a fourth permeate stream;
(g) discharging the fourth permeate stream from the fourth permeate port;
(h) discharging the fourth non-permeate stream from each of the at least one stripping membrane module through the fourth non-permeate port;
(i) sweeping and discharging the fourth permeate stream from the fourth permeate port using a sweep gas that is fed in a first direction of flow that is countercurrent to a second direction of flow that the first non-permeate stream is fed into the at least one stripping membrane module in step (e);
(j) compressing the first permeate stream in a first compressor to form a compressed first permeate stream;
(k) feeding the compressed first permeate stream to at least one second stage membrane module, each of the at least one second stage membrane module having a second high pressure side and a second low pressure side, the second high pressure side extending from a second feed port to a second non-permeate port, the second low pressure side being in fluid flow communication with a second sweep port and a second permeate port;
(l) separating the compressed first permeate stream in the at least one second stage membrane module into a second non-permeate stream and a second permeate stream;
(m) discharging the second non-permeate stream from each of the at least one second stage membrane module through the second non-permeate port;
(n) discharging the second permeate stream from each of the at least one second stage membrane module through the second permeate port;
(o) combining the second non-permeate stream with a compressed combined feed stream to form the pressurized feed gas stream;
(p) feeding the second permeate stream into at least one third stage membrane module, each of the at least one third stage membrane module having a third high pressure side and a third low pressure side, the third high pressure side extending from a third feed port to a third non-permeate port, the third low pressure side being in fluid flow communication with a third sweep port and a third permeate port;
(q) separating the second permeate stream in the at least one third stage membrane module into a third non-permeate stream and a third permeate stream;
(r) discharging the third non-permeate stream from each of the at least one third stage membrane module through the third non-permeate port;
(s) discharging the third permeate stream from each of the at least one third stage membrane module through the third permeate port;
(t) combining the third non-permeate stream with a raw feed gas stream to form a combined feed stream; and
(u) compressing the combined feed stream in a second compressor to form the compressed combined feed stream.

Aspect 19: The method of Aspect 18, wherein step (i) further comprises introducing the sweep gas at a pressure of less than 1.00 barg.

Aspect 20: The method of any of Aspects 18-19, wherein the sweep gas comprises an off-gas from a liquefaction process or a temperature swing adsorption process.

BRIEF DESCRIPTION OF THE DRAWINGS

FIG. 4 is a table setting forth the performance characteristics of the three-stage biogas separation system of FIG. 1;

FIG. 5 is a table setting forth the performance characteristics of the three-stage biogas separation system shown in FIG. 2.

DETAILED DESCRIPTION

Figure 1:
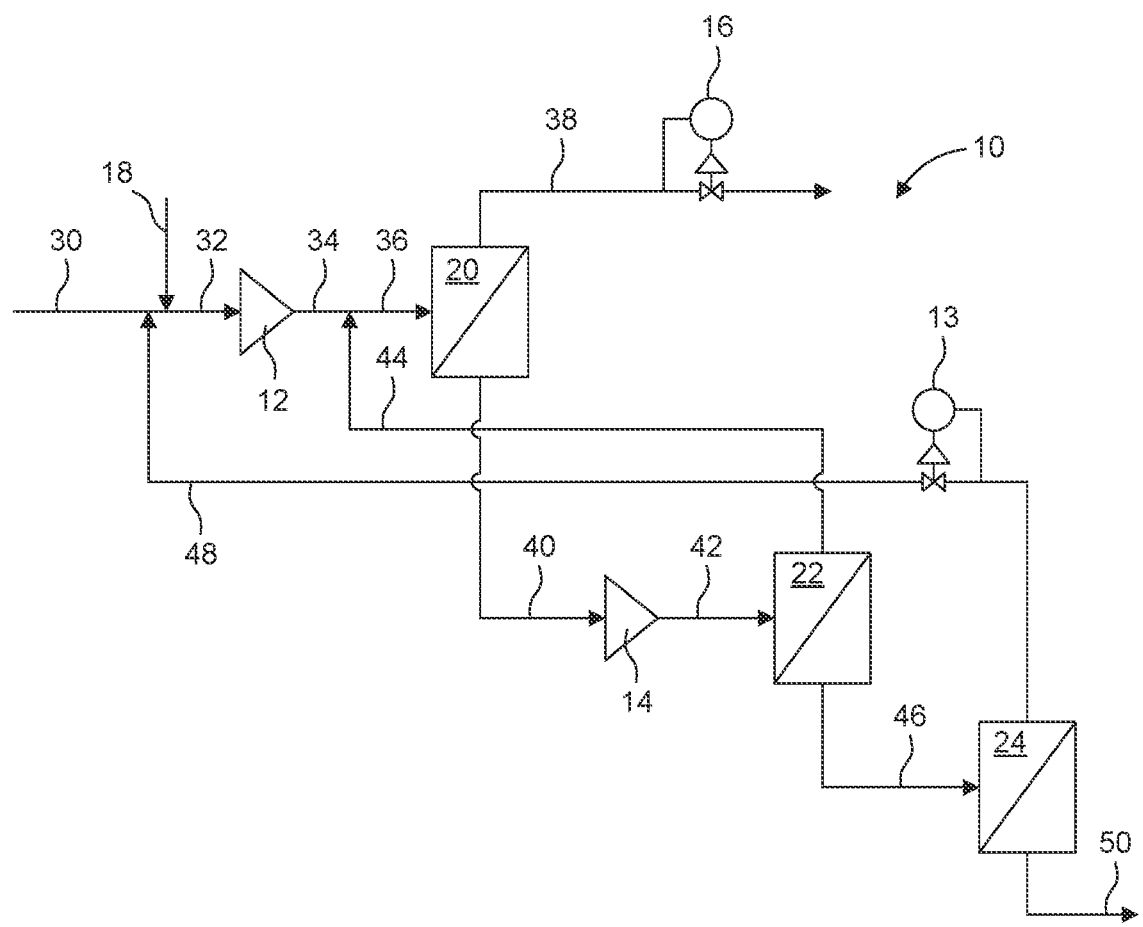
FIG. 1 is a process flow diagram of an exemplary three-stage biogas separation system.

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing the exemplary embodiments of the invention. Various changes may be made in the function and arrangement of elements without departing from the spirit and scope of the invention.

In order to aid in describing the invention, directional terms may be used in the specification and claims to describe portions of the present invention (e.g., upper, lower, left, right, etc.). These directional terms are merely intended to assist in describing and claiming the invention and are not intended to limit the invention in any way. In addition, reference numerals that are introduced in the specification in association with a drawing figure may be repeated in one or more subsequent figures without additional description in the specification in order to provide context for other features.

In the claims, letters are used to identify claimed steps (e.g. (a), (b), and (c)). These letters are used to aid in referring to the method steps and are not intended to indicate the order in which claimed steps are performed, unless and only to the extent that such order is specifically recited in the claims.

Unless otherwise indicated, the articles "a" and "an" as used herein mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "biogas", as used in the specification and claims, means a renewable fuel produced by the breakdown of organic matter, for example food scraps or animal waste.

The term "sweep gas", as used in the specification and claims, means a stream of gas which is supplied to the low pressure side of the membrane and dilutes the permeate gas, reducing its partial pressure, further assisting in the removal of permeate gas from the membrane.

The term "membrane", as used in the specification and claims, means an interphase between two adjacent phases acting as a selective barrier, regulating the transport of gases among gas mixtures.

The term "off-gas", as used in the specification and claims, means a gas that is produced or given off, especially one emitted as the byproduct of a chemical process.

The term "biomethane product", as used in the specification and claims, means refined biogas that has been enriched to at least 95% methane.

The term "thermal swing adsorption", as used in the specification and claims, means a separation process that makes use of the thermodynamic characteristics of an adsorbate.

The term "membrane module", as used in the specification and claims, means a device that is used to selectively separate gases by flowing, at a relatively high pressure, a feed gas through one or more conduits contained within a shell (also referred to as a high pressure side). The conduits are at least partially defined by a membrane material that provides a barrier between each conduit and a shell space (also referred to as a low pressure side). The shell space is an internal volume within the shell and external to each of the membranes that is maintained at a relatively low pressure. The shell side is in fluid flow communication with a permeate port, through which gas that permeates the membrane(s) exits the shell. Optionally, a sweep port may also be provided, which supplies a sweep gas to the shell space and assists the flow of permeate gas through the permeate port. The membrane material is chosen to enable one or more gases in the feed stream (referred to as the permeate gas) to pass through the membrane material at a higher rate than other gas(es) in the feed stream (referred to as the non-permeate or product gas).

FIG. 1 is an exemplary three-stage membrane biogas separation system 10, which includes two compressors 12 and 14. Biogas typically comprises carbon dioxide ($CO_2$) and methane ($CH_4$) as major constituents, often along with other minor constituents such as oxygen ($O_2$) and nitrogen ($N_2$). Membranes used in system 10 are typically selective for $CO_2$ over $CH_4$, meaning that $CO_2$ is considered a fast permeating gas that preferentially crosses the membrane at a relatively high rate, while $CH_4$ is a slow permeating gas that crosses the membrane at a relatively low rate. Hereinafter, a fast permeating gas and a slow permeating gas may be referred to a fast gas and a slow gas, respectively. Gas permeability through a membrane is governed by the solution-diffusion transport mechanism where the permeation rate is a function of the molecular size (diffusivity) and the molecular solubility in the polymer and is proportional to the driving force. The driving force for gas separation is the partial pressure differential of the permeating species between the high pressure and low pressure sides of the membrane. The gas permeability of each gaseous component of a gas mixture will typically be different, and the partial pressure of each gaseous component will be proportional to its relative concentration in the gas mixture as well as the total pressure of the gas mixture.

In system 10, a third non-permeate stream 48 (discussed below) is mixed into the raw feed gas stream 30 to form a combined feed stream 32. The raw feed gas stream may be obtained from a number of sources; one such source being a biogas resulting from biological fermentation of organic solids during anaerobic digestion. A typical composition of a biogas raw feed gas stream would be 40-70% $CH_4$, 30-60% $CO_2$, saturated with water vapor, and low concentrations of hydrogen sulfide (0-5 ppm), nitrogen (0-5%), and oxygen (0-5%). The combined feed stream 32 is compressed to a higher pressure in a feed compressor 12 to yield a compressed combined feed stream 34. A second recycled stream 44 (also called a second non-permeate stream 44, as discussed below) is mixed into the compressed combined feed stream 34 to form a pressurized feed gas stream 36.

The pressurized feed gas 36, containing a mixture of slow and fast gases, is supplied to a first stage membrane 20. Gas comprising primarily fast gas plus a minority of slow gas permeates and exits the first stage membrane 20 as a first permeate stream 40, while gas comprising primarily slow gas plus a minority of fast gas that fails to permeate the membrane is rejected and withdrawn as a first non-permeate stream 38. In the case of biogas, CO2 would permeate much more rapidly than CH4. The first stage non-permeate stream 38 can be withdrawn as a final product stream of the slow gas, having a high concentration of the slow gas and a very low concentration of the fast gas. The first permeate stream 40 is re-compressed in a compressor 14, generating a compressed first stage permeate stream 42, which is fed to a second stage membrane 22 where additional slow gas is rejected and withdrawn as a second stage non-permeate stream 44, and the fast gas permeates the membrane, generating a second stage permeate stream 46. The second stage non-permeate stream 44 is mixed into the compressed combined feed stream 34 at a point downstream of the feed compressor 12. The second stage permeate stream 46 is fed to a third stage membrane 24, where the slow gas is rejected and withdrawn as a third stage non-permeate stream 48, and the fast gas permeates the membrane 24, and generates a waste stream 50. The third stage non-permeate stream 48 is returned to a point upstream of the feed compressor 12 where it is mixed into the raw feed gas stream 30, as discussed above, and is recycled through the system 10. Each membrane 20, 22, 24 may contain one or more membranes. If multiple membranes are used at each stage, they may be arranged in series or parallel, or both.

It is not uncommon for biogas generation systems to have low pressure off-gases with low CO2 concentration generated from other unit operations, such as tail gases from thermal swing adsorption (TSA) systems or liquefaction units. In system 10, an off-gas stream 18 is added to the combined feed stream 32 upstream from the feed compressor 12. In many applications, adding the off-gas stream 18 to the combined feed stream 32 increases the membrane area required to achieve the desired product purity. Additionally, the low pressure off-gas stream 18 often has a higher purity than the raw feed gas stream 30. Therefore, combining the two streams is not thermodynamically favorable.

Figure 2:
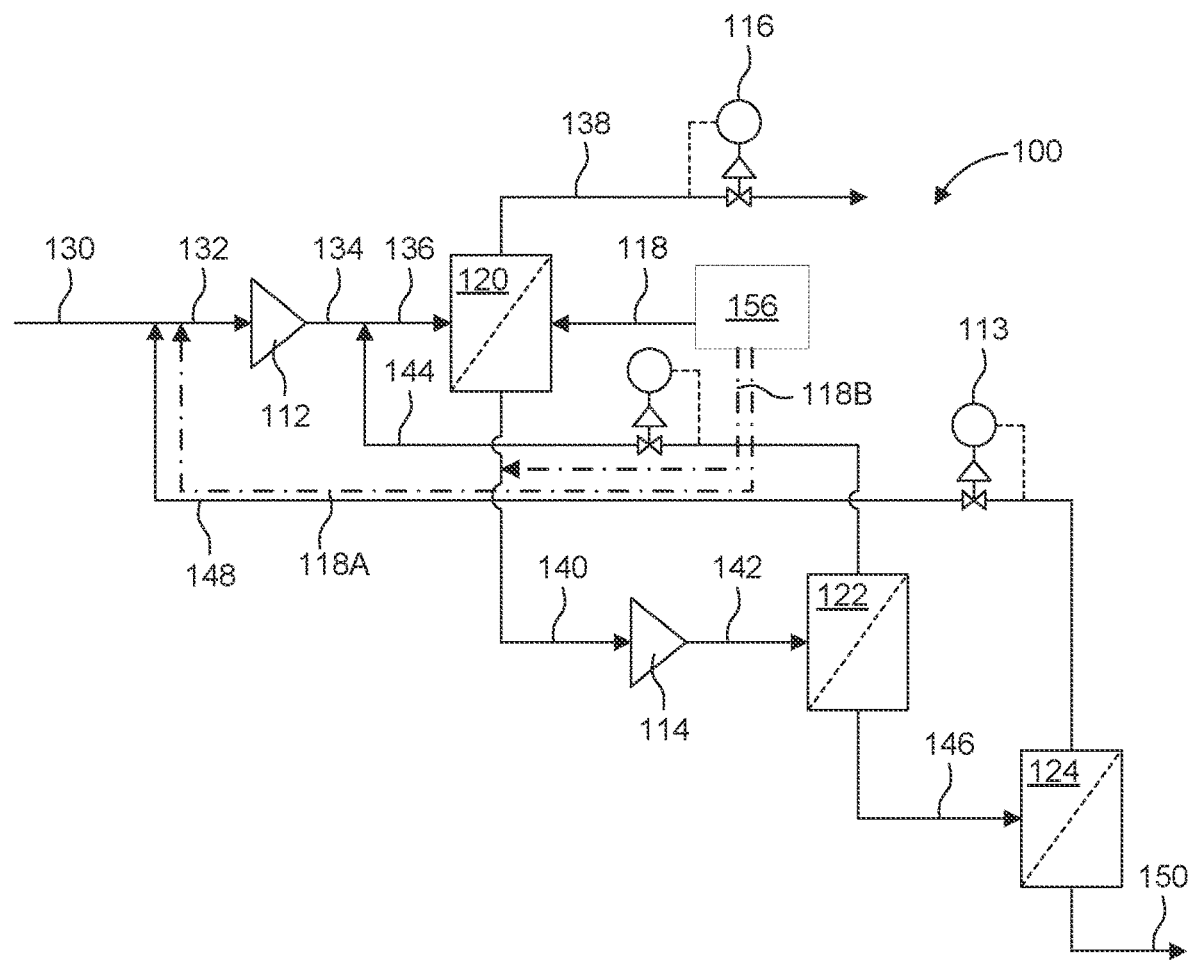
FIG. 2 is a process flow diagram of an exemplary three-stage membrane biogas separation system, wherein the first stage membrane includes an inlet for the introduction of an external sweep gas.

FIG. 2 shows an exemplary embodiment of a three-stage membrane biogas separation system 100. System 100 is substantially similar to system 10 of FIG. 1, but is modified to introduce the off-gas stream (shown schematically as coming from a source of off-gas 156) as a low pressure sweep gas stream 118 for the first stage membrane 120 instead of being added to the combined feed stream 132.

As with system 10, the membranes 120, 122, 124 used in the present system 100 are also selective for CO2 over CH4. In the system 100 of FIG. 2, a raw feed gas stream 130 containing a mixture of a fast gas and a slow gas (e.g., biogas containing CO2 and CH4) is fed into the system 100. For example, as with system 10, the raw feed gas may be obtained from biological fermentation of organic solids during anaerobic digestion. A first recycled stream 148 (also called a third non-permeate stream 148) is mixed into the raw feed gas stream 130 to form a combined feed stream 132. The combined feed stream 132 is compressed to a higher pressure in a feed compressor 112 to yield a compressed combined feed stream 134. A second recycled stream 144 (also called a second non-permeate stream 144) is mixed into the compressed combined feed stream 134 to form a pressurized feed gas stream 136 which contains a mixture of slow and fast permeating gases, and is supplied to the first stage membrane 120 that is selective for a fast gas over a slow gas. In the case of this biogas, CO2 would permeate much more rapidly than CH4. The first stage membrane 120 may include one or more membranes.

The composition of the low pressure sweep gas stream 118 is preferably 0-5% CO2 and less than 1% undesirable slow gases (such as nitrogen). The sweep gas stream 118 is fed to the first stage membrane 120 to sweep the shell side of the first stage membrane 120. Gas comprising primarily fast gas plus a minority of slow gas permeates and exits the first stage membrane 120 as a first permeate stream 140, while gas comprising primarily slow gas plus a minority of fast gas that fails to permeate the first stage membrane 120 is rejected and withdrawn as a first non-permeate stream 138. A control valve 116 may be used to regulate pressure of the first non-permeate stream 138 as it exits the system 100.

The first non-permeate stream 138 can be withdrawn as a final product stream of the slow gas, having a high concentration of the slow gas and a very low concentration of the fast gas. The first permeate stream 140 is re-compressed in a first stage permeate compressor 114, generating a compressed first permeate stream 142, i.e., a pressurized mixture of fast permeating gas with some amount of slow permeating gas, which is fed to a second stage membrane module 122, which may include one or more membranes. Gas comprising primarily fast gas plus a minority of slow gas permeates and exits the second stage membrane module 122 as a second permeate stream 146, while gas comprising slow and fast gas which fails to permeate the membrane is rejected and withdrawn as the second non-permeate stream 144. The second non-permeate stream 144 is recycled back into the compressed combined feed stream 134 downstream of the feed compressor 112.

The second permeate stream 146 is fed to a third stage membrane 124. In the third stage membrane 124, gas comprising primarily fast gas plus a minority of slow gas permeates and exits the third stage membrane 124 as a third permeate stream 150, while the slow gas is rejected and withdrawn as a third stage non-permeate stream 148. The third non-permeate stream 148 is recycled back into the raw feed gas stream 130 upstream of the feed compressor 112. A control valve 113 is used to maintain appropriate pressure across the third stage membrane 124 and may be used to influence pressure on the shell side of the second stage membrane module 122. The third permeate stream 150 (also referred to as a vent stream 150) is a fast-gas rich stream, which in the case of biogas would be primarily CO2, that can be vented or processed further depending on the application. The third stage membrane 124 may include one or more membranes. Each membrane stage 120, 122, and 124 may contain one or more membranes, with multiple membranes being arranged in series or parallel.

The system 100 can be used to separate any one of several fast gas/slow gas pairs in a feed stream 130, including, but not limited to: CO2/CH4, H2/CO, H2/CO2, CO2/N2, O2/N2, He/CH4, H2/CH4, and H2/N2.

In some applications, it may be desirable to provide the ability to introduce portions of the off-gas 156 into different streams of the system 100 in a controlled way. For example, it may be desirable to introduce a first portion 118A of the off-gas 156 into the combined feed stream 132 upstream from the feed compressor 112 and/or a second portion 118B of the off-gas 156 into the first permeate stream 140 upstream from the first stage permeate compressor 114. The fraction of the off-gas 156 being directed to each of the streams 118, 118A, and 118B can be adjusted to balance the power required to drive the feed compressor 112 and the first stage permeate compressor 114.

Figure 6:
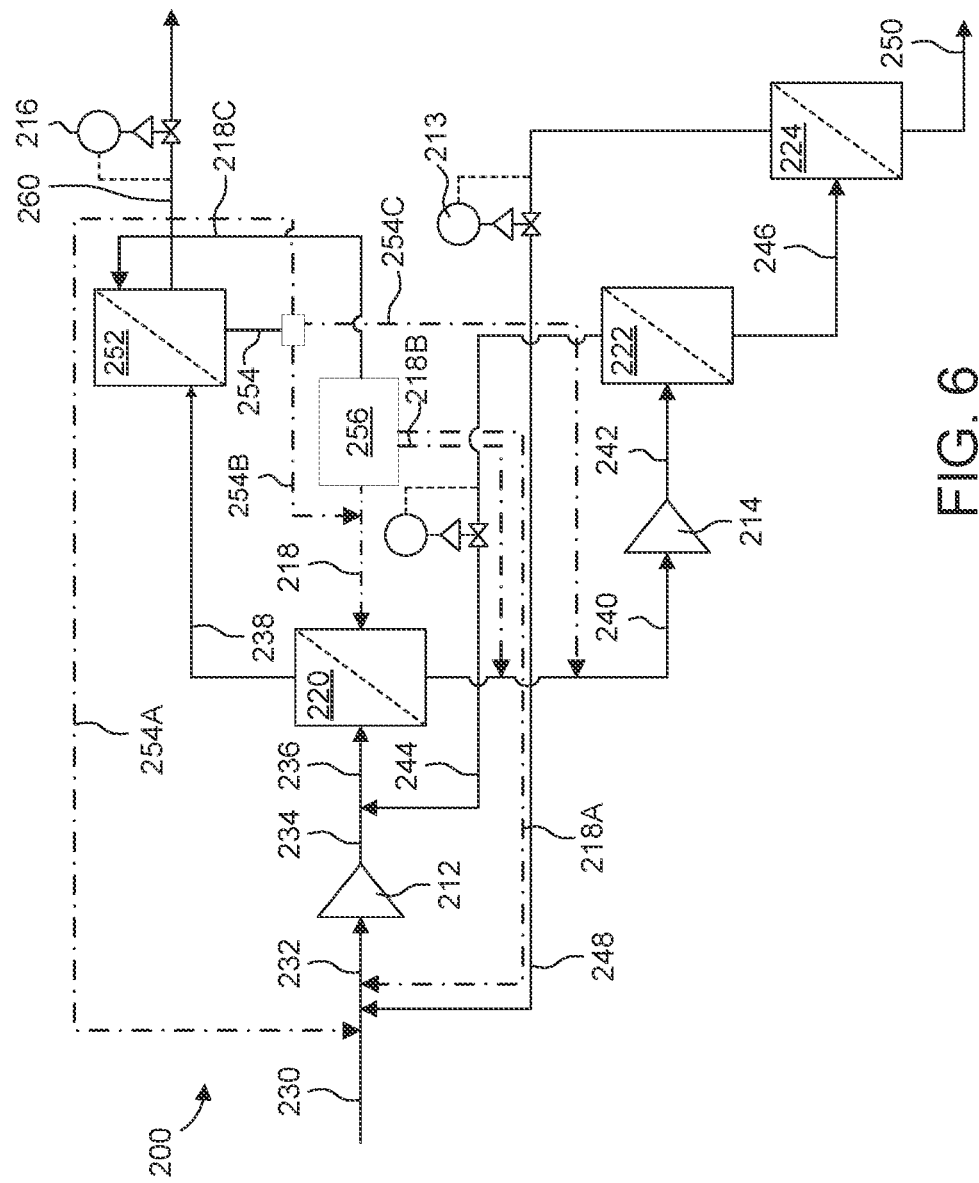
FIG. 6 is a process flow diagram of another exemplary three-stage membrane biogas separation system, which includes a stripping stage.

FIG. 6 shows another exemplary embodiment of a three-stage membrane biogas separation system 200. System 200 is substantially similar to system 100 of FIG. 2, but is modified to introduce a stripping stage, comprising a stripping membrane 252 into which the first non-permeate stream 238 is fed. This embodiment may be used in applications in which very low CO2 concentrations are desired in the product gas. In this embodiment, elements shared with the first embodiment (system 100 of FIG. 2) are represented by reference numerals increased by factors of 100. For example, the feed compressor 112 in FIG. 2 corresponds to the feed compressor 216 in FIG. 6. In the interest of brevity in the specification, some features of this embodiment that are shared with the first embodiment are numbered in FIG. 6, but are not repeated in the specification.

In the stripping membrane 252, gas comprising a mixture of fast and slow permeating gases permeates and exits the stripping membrane 252 as a fourth permeate stream 258, while the slow gas is rejected and withdrawn as a stripped non-permeate stream 260. A control valve 216 may be used to regulate pressure of the stripped non-permeate stream 260 as it exits the system 200. A stripped permeate stream 254, comprising primarily a mixture of fast and slow permeating gases permeates and exits the stripping membrane 252. Either all or portions of the stripped permeate stream 254 could be directed to one or more streams in the system 200. For example, a portion 254A could be recycled into the compressed feed stream 234 upstream from the feed compressor 212, a portion 254B could be combined with the sweep gas 218 before being flowed into the shell side of the first stage membrane 220, and/or a portion 254C could be fed to the inlet of the first stage permeate compressor 214.

In most applications, sweep gas would only be supplied to the low pressure side of the membrane module stage that is providing the final product gas stream. Generally, the product gas stream is the stream having the highest concentration of the product gas (in the examples provided herein, CH4) of any stream in the system. In system 100, the first non-permeate stream 138 is the final product stream (also referred to as a biomethane product). Accordingly, in system 100, the sweep gas stream 118 is supplied to the low pressure side of the first stage membrane module 120. In system 200, the stripped non-permeate stream 260 is the product gas stream. Accordingly, the sweep gas 218C is supplied to the low pressure side of the stripping membrane module 252.

Figure 3:
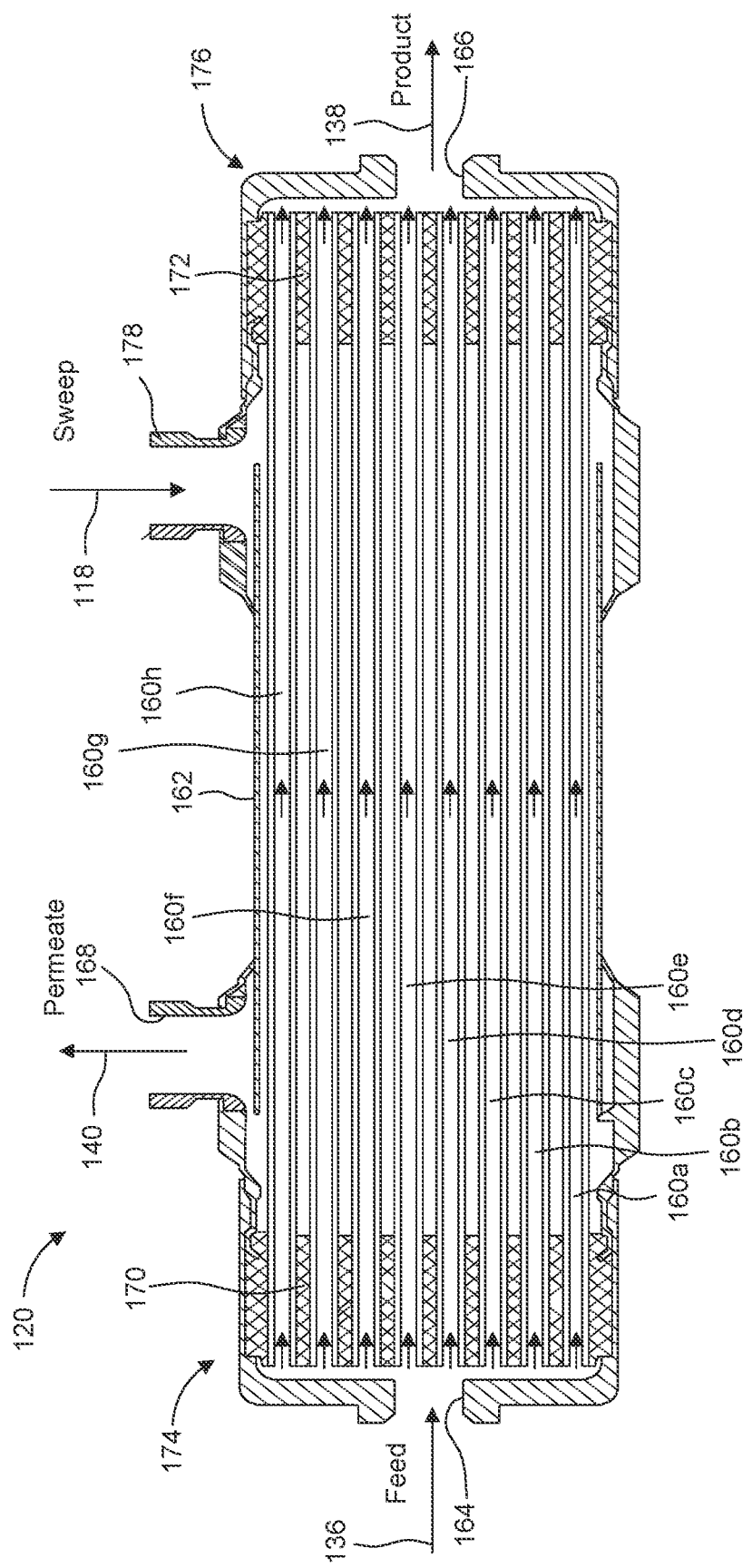
FIG. 3 is a sectional view illustrating the internal structure of the exemplary gas separation membrane.

Referring now to FIG. 3, structural details of an exemplary first stage membrane 120 are shown. Similar structure could be used for any of the membranes 120, 122, 124 used in the system 100. The first stage membrane 120 comprises a core having a bundle of open-ended hollow fibers 160a-h that extend along the length of a shell 162. The shell 162 includes a feed port 164 through which the pressurized feed gas stream 136 is fed, a non-permeate port 166 through which the first non-permeate stream 138 exits the first stage membrane 120, and a permeate port 168 through which the first permeate stream 140 exits the first stage membrane 120.

The bundle of hollow fibers 160a-h is held together at both ends by a tubesheet 170, 172, made of thermoplastic or thermoset materials. Examples of tubesheet materials include cured epoxy or polyurethane-based formulations. One of the tubesheets 170 is located at a feed end 174 of the first stage membrane 120 (adjacent to the feed port 164) and the other tubesheet 172 is located at a non-permeate end 176 of the first stage membrane 120 (adjacent to the non-permeate port 166).

In order to provide counterflow between the pressurized feed gas stream 136 and the first permeate stream 140, the permeate port 168 is located inboard of the feed end tubesheet 170 and typically no more than ⅓ of the distance from the inner edge of the feed end tubesheet 170 to the non-permeate end tubesheet 172. Similarly, a sweep port 178 is located inboard of the non-permeate end tubesheet 172 and typically no more than ⅓ of the distance from the inner edge of the non-permeate end tubesheet 172. The sweep port 178 may be in fluid flow communication with a supply of the sweep gas 118.

The fibers 160a-h have semi-permeable walls that are intended to be permeable to the fast gases and less permeable to slow gases. Accordingly, when the pressurized feed gas stream 136, which is a mixture of slow and fast gases, flows through the fibers 160a-h, the fast gas passes through the walls of the fibers 160a-h and flows through the permeate port 168 and the slow gas remains within the fibers 160a-h and flows to the non-permeate port 166.

A bore side of the first stage membrane 120 is defined herein as the path the fluid follows when introduced through the feed port 164, through the bore or lumen side of the fibers 160a-h (shown by the arrows in FIG. 3), and exits through the non-permeate port 166. A shell side of the first stage membrane 120 is defined herein as an internal volume within the shell 162, between the tubesheets 170, 172, and external to the fibers 160a-h. In the system 100, the pressurized feed gas stream 136 flows into the bore side of the first stage membrane 120 and exits the bore side as the first non-permeate stream 138. After passing through the walls of the fibers 160a-h, the fast gas portion of the pressurized feed gas stream 136 enters the shell side, where it is optionally mixed with a sweep gas 118, and is swept out of the shell side through the permeate port 168 as the first permeate stream 140.

The sweep gas stream 118 may be introduced at a low pressure of less than 1.00 barg, e.g., 0.89 barg. The sweep gas stream 118 may be provided at a concentration of CO2 less than 15%, or less than 10%, or less than 5%. The sweep gas stream 118 may be provided at a concentration of CH4 that is greater than 85%, or greater than 90%, or greater than 95%. The sweep gas stream 118 may be provided with a molar flow rate of contained nitrogen that is less than or equal to 5% of the total molar flow rate of the raw feed gas in stream 130. The sweep gas stream 118 may be provided with a molar flow rate of contained oxygen that is less than or equal to 5% of the total molar flow rate of the raw feed gas in stream 130.

In the system 100, each membrane stage 120, 122, and 124 may contain one or more membranes, with multiple membranes being arranged in series and/or parallel. Each membrane may be in the form of flat sheets or hollow fibers, and modules of membranes may be either a spiral wound flat sheet or a bundle of hollow fibers. It is not necessary for each membrane stage 120, 122, and 124 to use the same number and/or type of membrane. For example, in some embodiments, all three stages use may use membranes of the same permeability and selectivity. In other embodiments, the membrane permeability and selectivity of each stage may be different from that in other stages. In yet other embodiments, two stages may use membranes of the same permeability and selectivity and the remaining stage may use membranes of a different permeability and selectivity. Each membrane may be made of a single polymer selected from the numerous polymers known in the art or future determined to be suitable for the desired separation, or each membrane may be a composite membrane made from multiple polymers.

It should be understood that other types of membrane modules could be used. Examples of membrane configurations include hollow fibers packaged as membrane bundles, flat sheets, or spiral wound, as well as plate and frame configurations. Membranes are commonly formed from polymers. Examples of polymers used to make membranes include, but are not limited to, polystyrene, polysulfone, polyethersulfone, polyvinyl fluoride, polyvinylidene fluoride, polyether ether ketone, polycarbonate, polyphenylene oxide, polyethylene, polypropylene, cellulose acetate, polyimide (such as Matrimid 5218 or P-84), polyamide, polyvinyl alcohol, polyvinyl acetate, polyethylene oxide, polydimethylsiloxane, copolymers, block copolymers, or polymer blends. Hollow fiber membranes may be asymmetric with a nonporous layer or may contain a porous support with a nonporous coating. A coating may be applied to the inner or outer surface of the hollow fiber. Membranes in which bundles of hollow fibers are held together at one or both ends by a tubesheet (such as the membrane 120 of FIG. 3), the tubesheet may be made of thermoplastic or thermoset materials. Examples of tubesheet materials include cured epoxy or polyurethane-based formulations. The vessel may be constructed of plastic, metal or other suitable materials.

In embodiments in which a bundle of hollow fibers is provided (such as the membrane 120 of FIG. 3), the feed gas may be fed through the bore side of the fibers (as shown in FIG. 3). Alternatively, the feed gas could be fed through the shell space. In this case, the shell space would become the high pressure side of the membrane, the bore space would become the low pressure side of the membrane, the sweep port 178 and the permeate port 168 would become the feed and product ports, and the feed port 164 and non-permeate port 166 would become the sweep port and permeate port, respectively.

The tables of FIGS. 4 and 5 compare the performance characteristics of the three-stage biogas separation of system 10 (FIG. 1) which adds the off-gas stream to the combined feed stream 32, with the performance characteristics of the three-stage biogas separation of system 100 (FIG. 2), which uses the off-gas stream as a sweep gas stream 118 for the first stage membrane 120. Simulations were performed using the conditions set forth in Table 1 below:

TABLE 1

Raw feed: 500 NMH at 60% CH4/40% CO2
Operating temperature: 40° C.
First compressor outlet pressure: 13 barg
Second compressor outlet pressure: 13.9 barg
TSA tail gas: 200 NMH at 95% CH4/5% CO2
Target: 98.5% CH4 in biomethane product
Target: 1% CH4 in vent stream
CO2/CH4 selectivity = 30

As demonstrated in FIGS. 4 and 5, and as summarized in Table 2 below, both the system 10 and system 100 produce the target product composition and target product recovery. However, utilizing the sweep gas stream 118, the present system 100 achieves the same result utilizing 75% of the membrane area required under the system 10 for the conditions described above.

TABLE 2

| | System 100 (FIG. 2) | System 10 (FIG. 1) |
|---|---|---|
| Product Composition | 98.5% CH4 in biomethane product 38; 1% CH4 in vent stream 50 | 98.5% CH4 in biomethane product 138; 1% CH4 in vent stream 150 |
| Product Recovery | 99.58% CH4 | 99.58% CH4 |
| Total Relative membrane area | 0.75 | 1.0 |

As shown in FIG. 4, a process simulation was performed using the configuration of system 10 having three membranes stages 20, 22, and 24, a feed compressor 12 and a first stage permeate compressor 14. Under this process simulation, the low pressure off-gas is supplied at a point upstream of the compressor and not as a sweep gas system 10. A feed of 500 NMH of a raw biogas stream 30 containing 60% CH4 and 40% CO2 is provided to the system. The feed stream 30 is combined with the third non-permeate stream 48 having a flow rate of 20.2 NMH and containing 56.12% CH4 and 43.88% CO2 and with the low pressure off-gas having a flow rate of 200 NMH and containing 95.00% CH4 and 5.00% CO2 to form the combined feed stream 32 which is compressed by compressor 12. The resultant compressed combined feed stream 34 is combined with the second non-permeate stream 44 at 250.8 NMH and containing 62.17% CH4 and 37.83% CO2 to create a pressurized feed gas stream 36 of 971.1 NMH containing 67.69% CH4 and 32.31% CO2 at approximately 13.00 barg and 40.0° C. The compressed combined feed stream 36 is fed to the first stage membrane 20 to generate the first non-permeate stream 38 and the first permeate stream 40. The first non-permeate stream 38 has a molar flow rate of 495.4 NMH, containing 98.5% CH4 and 1.5% CO2 and is withdrawn as the product gas.

The first permeate stream 40 has a molar flow rate of 475.7 NMH entering the first permeate compressor 14. The pressurized feed gas stream 42 is fed to the second stage membrane 22 to generate the second non-permeate stream 44 and the second permeate stream 46. The second permeate stream 46 is fed to the third stage membrane, and the third stage permeate stream 50 (or waste stream) is withdrawn at 204.6 NMH and contains just 1.00 mol% CH4 and 99.0% CO2.

By comparison, FIG. 5 sets forth a process simulation performed using the configuration of the system 100, which utilizes the low pressure off-gas as a sweep gas stream 118. The system 100 includes three stage membranes 120, 122, and 124, a feed compressor 112, and a first stage permeate compressor 114. A feed of 500 NMH of a raw biogas stream 130 containing 60% CH4 and 40% CO2 is provided to the system 100. The stream 130 is combined with the third non-permeate stream 148 having a flow rate of 28.8 NMH and containing 46.85% CH4 and 53.15% CO2 to form the combined feed stream 132, which is compressed by compressor 112. The resultant compressed combined feed stream 134 is combined with the second non-permeate stream 144 at 463.4 NMH and containing 59.57% CH4 and 40.43% CO2 to create a pressurized feed gas stream 136 of 992.2 NMH containing 59.42% CH4 and 40.58% CO2 at approximately 13.00 barg and 40° C. The pressurized feed gas stream 136 is fed to the first stage membrane 120 to generate the first non-permeate stream 138 and the first permeate stream 140.

At the same time, a sweep gas stream 118 containing 95.00% CH4 and 5.00% CO2 is fed into the first stage membrane module 120. Due to the introduction of the sweep gas stream 118, the target product composition and target product recovery is achieved with only 75% of the area required in the system 10. The first non-permeate stream 138 contains 98.5% CH4 and 1.5% CO2 and is withdrawn as the product gas.

The first permeate stream 140 has a molar flow rate of 696.8 NMH entering the first stage permeate compressor 114. The compressed first permeate stream 142 is fed to the second stage membrane module 122 to generate the second non-permeate stream 144 and the second permeate stream 146. The second permeate stream 146 is fed to the third stage membrane module 124, and a third stage permeate stream 150 (or waste stream) is withdrawn at 204.6 NMH and contains just 1.00 mol% CH4 and 99.0% CO2.

The present invention is not to be limited in scope by the specific aspects or embodiments disclosed in the examples which are intended as illustrations of a few aspects of the invention and any embodiments that are functionally equivalent are within the scope of this invention. Various modifications of the invention in addition to those shown and described herein will become apparent to those skilled in the art and are intended to fall within the scope of the appended claims.

The invention claimed is:

1. A method comprising:
   (a) compressing a feed gas stream to form a pressurized feed gas stream;
   (b) feeding the pressurized feed gas stream into at least one first stage membrane module, each of the at least one first stage membrane module having a first high pressure side and a first low pressure side, the first high pressure side extending from a first feed port to a first non-permeate port, the first low pressure side being in fluid flow communication with a first sweep port and a first permeate port;
   (c) separating the pressurized feed gas stream in each of the at least one first stage membrane module into a first non-permeate stream and a first permeate stream;
   (d) sweeping and discharging the first permeate stream from the first permeate port using a sweep gas that is fed in a first direction of flow that is countercurrent to a second direction of flow that the pressured feed gas stream is fed into the at least one first stage membrane module in step (a);
   (e) discharging the first non-permeate stream from each of the at least one first stage membrane module through the first non-permeate port;
   (f) compressing the first permeate stream in a first compressor to form a compressed first permeate stream;
   (g) feeding the compressed first permeate stream to at least one second stage membrane module, each of the at least one second stage membrane module having a second high pressure side and a second low pressure side, the second high pressure side extending from a second feed port to a second non-permeate port, the second low pressure side being in fluid flow communication with a second sweep port and a second permeate port;
   (h) separating the compressed first permeate stream in the at least one second stage membrane module into a second non-permeate stream and a second permeate stream;
   (i) discharging the second non-permeate stream from each of the at least one second stage membrane module through the second non-permeate port;
   (j) discharging the second permeate stream from each of the at least one second stage membrane module through the second permeate port;
   (k) combining the second non-permeate stream with a compressed combined feed stream to form the pressurized feed gas stream;
   (l) feeding the second permeate stream into at least one third stage membrane module, each of the at least one third stage membrane module having a third high pressure side and a third low pressure side, the third high pressure side extending from a third feed port to a third non-permeate port, the third low pressure side being in fluid flow communication with a third sweep port and a third permeate port;
   (m) separating the second permeate stream in the at least one third stage membrane module into a third non-permeate stream and a third permeate stream;
   (n) discharging the third non-permeate stream from each of the at least one third stage membrane module through the third non-permeate port;
   (n) discharging the third permeate stream from each of the at least one third stage membrane module through the third permeate port;
   (o) combining the third non-permeate stream with a raw feed gas stream to form a combined feed stream; and
   (p) compressing the combined feed stream in a second compressor to form the compressed combined feed stream.

2. The method of claim 1, wherein step (d) further comprises introducing the sweep gas at a pressure of less than 1.00 barg.

3. The method of claim 1, wherein the sweep gas comprises less than 15% carbon dioxide.

4. The method of claim 1, wherein the sweep gas comprises at least 85% methane.

5. The method of claim 1, wherein the sweep gas provides a first molar flow rate of nitrogen that is less than or equal to 5% of a second molar flow rate of the pressurized feed gas stream.

6. The method of claim 1, wherein the sweep gas comprises an off-gas.

7. The method of claim 6, wherein the off-gas comprises an off-gas from a liquefaction process or a temperature swing adsorption process.

8. The method of claim 1, wherein the sweep gas comprises a tail gas from a thermal swing adsorption (TSA) process.

9. The method of claim 7, further comprising directing at least a portion of the off-gas to one or more selected from the group of: (1) the feed gas stream and (2) the first permeate stream.

10. The method of claim 1, wherein the at least one first stage membrane module comprises a plurality of membrane modules arranged in series and/or parallel.

11. The method of claim 1, wherein the at least one second stage membrane module comprises a plurality of membrane modules arranged in series and/or parallel.

12. The method of claim 1, wherein the at least one third stage membrane module comprises a plurality of membrane modules arranged in series and/or parallel.

13. The method of claim 1, wherein the feed gas stream is a product stream from an anaerobic digester.

14. The method of claim 1, wherein the feed gas stream comprises at least 40% methane.

15. The method of claim 1, wherein step (f) further comprises compressing the first permeate stream in the first compressor to a pressure of at least 10 barg to form the compressed first permeate stream.

16. The method of claim 1, wherein the first non-permeate stream comprises at least 70% methane.

17. The method of claim 1, wherein the third permeate stream comprises less than 1% methane.

18. A method comprising:
(a) compressing a feed gas stream to form a pressurized feed gas stream;
(b) feeding the pressurized feed gas stream into at least one first stage membrane module, each of the at least one first stage membrane module having a first high pressure side and a first low pressure side, the first high pressure side extending from a first feed port to a first non-permeate port, the first low pressure side being in fluid flow communication with a first sweep port and a first permeate port;
(c) separating the pressurized feed gas stream in each of the at least one first stage membrane module into a first non-permeate stream and a first permeate stream;
(d) discharging the first non-permeate stream from each of the at least one first stage membrane module through the first non-permeate port;
(e) feeding the first non-permeate stream into at least one stripping membrane module, each of the at least one stripping membrane module having a fourth high pressure side and a fourth low pressure side, the fourth high pressure side extending from a fourth feed port to a fourth non-permeate port, the fourth low pressure side being in fluid flow communication with a fourth permeate port;
(f) separating the first non-permeate stream in each of the at least one stripping membrane module into a fourth non-permeate stream and a fourth permeate stream;
(g) discharging the fourth permeate stream from the fourth permeate port;
(h) discharging the fourth non-permeate stream from each of the at least one stripping membrane module through the fourth non-permeate port;
(i) sweeping and discharging the fourth permeate stream from the fourth permeate port using a sweep gas that is fed in a first direction of flow that is countercurrent to a second direction of flow that the first non-permeate stream is fed into the at least one stripping membrane module in step (e);
(j) compressing the first permeate stream in a first compressor to form a compressed first permeate stream;
(k) feeding the compressed first permeate stream to at least one second stage membrane module, each of the at least one second stage membrane module having a second high pressure side and a second low pressure side, the second high pressure side extending from a second feed port to a second non-permeate port, the second low pressure side being in fluid flow communication with a second sweep port and a second permeate port;
(l) separating the compressed first permeate stream in the at least one second stage membrane module into a second non-permeate stream and a second permeate stream;
(m) discharging the second non-permeate stream from each of the at least one second stage membrane module through the second non-permeate port;
(n) discharging the second permeate stream from each of the at least one second stage membrane module through the second permeate port;
(o) combining the second non-permeate stream with a compressed combined feed stream to form the pressurized feed gas stream;
(p) feeding the second permeate stream into at least one third stage membrane module, each of the at least one third stage membrane module having a third high pressure side and a third low pressure side, the third high pressure side extending from a third feed port to a third non-permeate port, the third low pressure side being in fluid flow communication with a third sweep port and a third permeate port;
(q) separating the second permeate stream in the at least one third stage membrane module into a third non-permeate stream and a third permeate stream;
(r) discharging the third non-permeate stream from each of the at least one third stage membrane module through the third non-permeate port;
(s) discharging the third permeate stream from each of the at least one third stage membrane module through the third permeate port;
(t) combining the third non-permeate stream with a raw feed gas stream to form a combined feed stream; and
(u) compressing the combined feed stream in a second compressor to form the compressed combined feed stream.

19. The method of claim 18, wherein step (i) further comprises introducing the sweep gas at a pressure of less than 1.00 barg.

20. The method of claim 18, wherein the sweep gas comprises an off-gas from a liquefaction process or a temperature swing adsorption process.

* * * * *